United States Patent [19]

Golay

[11] 4,038,053

[45] July 26, 1977

[54] METHOD AND APPARATUS FOR INTRODUCING LIQUID SAMPLES INTO A GAS CHROMATOGRAPHIC COLUMN

[75] Inventor: Marcel J. E. Golay, Clair-Azur, Switzerland

[73] Assignee: The Perkin-Elmer Corporation, Norwalk, Conn.

[21] Appl. No.: 694,809

[22] Filed: June 10, 1976

[51] Int. Cl.² .......................................... B01D 15/08
[52] U.S. Cl. .......................................... 55/160; 55/67; 55/197
[58] Field of Search .................... 55/67, 197, 386, 160; 73/422 GC

[56] References Cited

U.S. PATENT DOCUMENTS

| | | | |
|---|---|---|---|
| 3,364,659 | 1/1968 | Pierrard et al. | 55/197 |
| 3,365,951 | 1/1968 | Jentzsch et al. | 55/197 X |
| 3,366,149 | 1/1968 | Taft et al. | 55/197 X |
| 3,668,834 | 6/1972 | Deans | 55/67 |
| 3,920,420 | 11/1975 | Valentin et al. | 55/67 |

*Primary Examiner*—John Adee
*Attorney, Agent, or Firm*—S. A. Giarratana; F. L. Masselle; E. T. Grimes

[57] ABSTRACT

The invention is directed to method and apparatus for introducing liquid samples into a gas chromatographic column by supplying a liquid sample to a heated injector in a continuous, uniform and relatively slow-moving flow; vaporizing the sample in the heated injector; passing the vapor through a supply line in the injector to a restrictor, vented to the atmosphere, until stationary conditions have been established; and then passing the vapor to the gas chromatographic column for sampling by reversing the flow in the supply line for a relatively short time.

6 Claims, 2 Drawing Figures

METHOD AND APPARATUS FOR INTRODUCING LIQUID SAMPLES INTO A GAS CHROMATOGRAPHIC COLUMN

BACKGROUND OF THE INVENTION

This invention relates to gas chromatography, and more particularly to a method and apparatus for introducing liquid samples into the carrier gas stream of a gas chromatograph.

Heretofore, sampling was effected by means of a hypodermic syringe, but the use of such a syringe involved some important disadvantages, as follows: (1) In spite of the fact that the sample was instantaneously injected, low-boiling point components vaporized more rapidly in the heated sampling system than the high-boiling point components. Therefore, withdrawal of part of the sample vapor for analytical purposes resulted in the sampling of a component mixture, whose component mixture ratios differed from those of the original sample. (2) The use of a syringe required a skilled operator. (3) Routine application of this syringe sampling method resulted in leakage of the injection membrane. (4) Inaccurate sampling quantities were introduced into the column. (5) The method was not very suitable for automated sampling injection.

In an attempt to overcome the foregoing problems, the patentee of U.S. Pat. No. 3,668,834 proposed a method of injecting a sample into a chromatographic column by passing a continuous stream of carrier gas through the column, passing a separate stream of a gas or liquid to be sampled, and diverting part of the separate stream into the carrier gas stream through an unrestricted sample injection limb, by varying the pressure difference across the limb. The present invention is an improvement over such prior art systems, as will become apparent as the description proceeds.

SUMMARY OF THE INVENTION

In order to accomplish the desired results this invention provides, in one form thereof, a new and improved method for introducing liquid samples into a gas chromatographic column, which includes the steps of supplying a liquid sample to a heated injector in a continuous, uniform and relatively slow-moving flow, and vaporizing the sample in the heated injector. The vapor is passed through a supply line in the injector to a by-passing restrictor until stationary conditions have been established and then the vapor is passed to the chromatographic column for sampling by reversing the flow in the supply line. According to one aspect of the invention, the step of supplying the liquid sample to the heated injector continues during the step of passing the vapor to the gas chromatographic column for sampling. Both said by-passing restrictor and said columns are also heated in order to maintain the samples in the gaseous state while flowing through.

In another form thereof the present invention provides a new and improved apparatus for introducing liquid samples into a gas chromatographic column which includes, in combination, means for supplying a liquid sample to a heating injector in a continuous, uniform and relatively slow-moving flow, and vaporizing the sample in the injector. According to one aspect of the invention, this means of supplying the liquid sample includes a cylinder having a dispensing outlet coupled to a supply line disposed in the heated injector, and an inlet coupled to a liquid sample source. A plunger is mounted in the cylinder and means are provided for rapidly reciprocating the plunger in the cylinder alternately to aspirate and evaporate in the heated injector and then vent said sample through a restrictor to the atmosphere, thereby to remove substantially all traces of the preceding sample. In addition, means are provided for slowly advancing the plunger in the cylinder to push the sample into the heated injector and thence for a relatively short time into the gas chromatographic column for sampling. It should be appreciated that means are provided for passing the vapor through the supply line in the injector to the restrictor until stationary conditions have been established and the passing the vapor to the gas chromatographic column by briefly reversing the flow in the supply line. According to one aspect of the invention, this last named means comprises a fluid bridge circuit having four arms including a first arm containing the gas chromatographic column, a second arm containing the aforementioned by-passing line restrictor, a third arm containing another line restrictor, and a fourth arm containing line restrictor means and means, such as solenoid controlled valve, for varying the resistance means. In addition, there is provided a first junction for coupling one end of the first arm with one end of the third arm and with one end of the supply line in the heated injector. A second couples one end of the second arm with one end of the fourth arem with the other end of the supply arm. A carrier gas source is coupled to the other end of the third and fourth arms, and control means are provided for by-passing the vapor through the supply line in the injector to the second arm until stationary conditions have been established and then passing it briefly through the supply line in the opposite direction to the first arm, containing the column.

DETAILED DESCRIPTION OF THE PREFERRED EMBODIMENT

Figure 1:
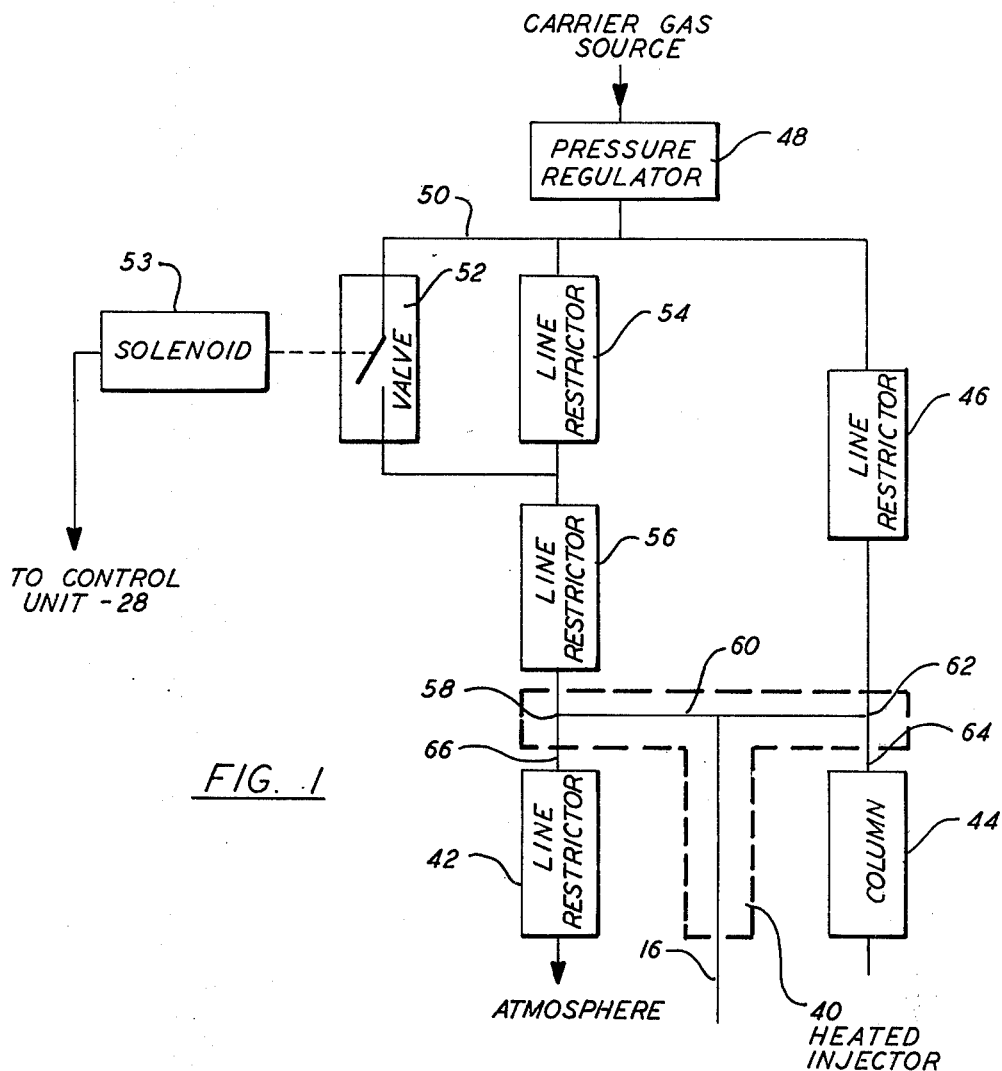
FIG. 1 is a schematic representation of a system for introducing liquid samples into a gas chromatograph according to the invention.
Figure 2:
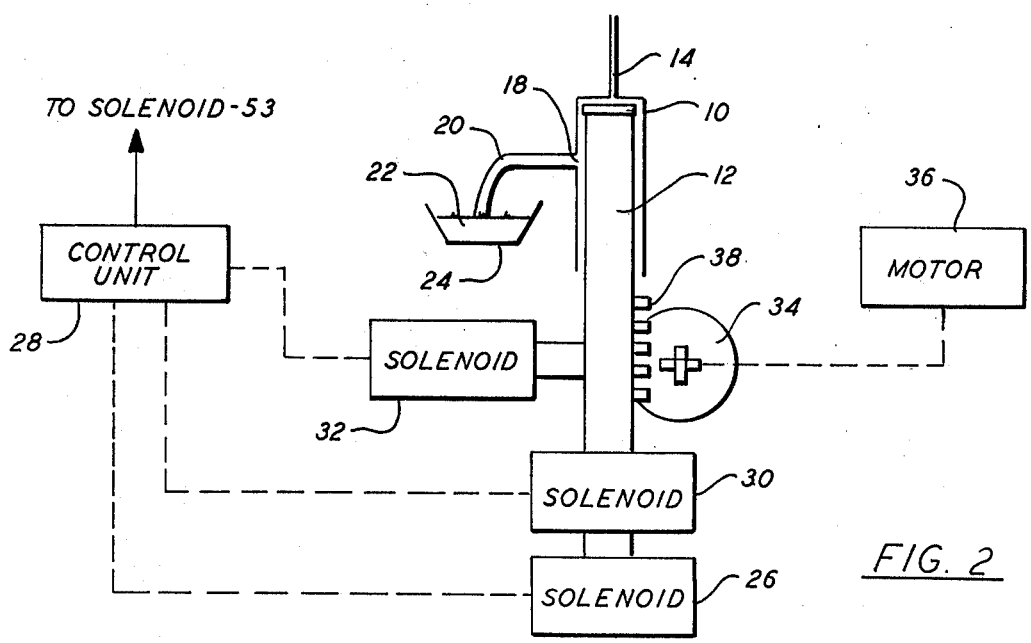
FIG. 2 is a schematic view of a pump system used with the system of FIG. 1

In the embodiment of the invention illustrated, a pump is employed, which includes a cylinder 10 having a plunger 12 mounted therein for sliding movement, the cylinder and plunger being in relatively tightly sealed relationship with respect to each other. The cylinder 10 is provided with an upper outlet 14, which is connected to an inlet tube 16, shown in FIG. 1, and a lower inlet 18 for receiving one end of an inlet nipple 20. The other end of the inlet nipple 20 is immersed in a sample 22 carried in a container 24. A solenoid 26 is provided, which is controlled by a control unit 28 for rapidly retracting the plunger 12. This action generates a vacuum in the cylinder above the plunger and in the outlet 14, as the inlet tube 16 is sized to have a preselected hydrodynamic resistance. The vacuum aspirates a portion of the sample 22 from the container 24, via the nipple 20, into the open portion of the cylinder 12 above the plunger. Thereafter, a solenoid 30, which is also controlled by the control unit 28, reverses the direction of and advances the plunger 12 to push the sample forward. This entire process, controlled by the control unit 28, is repeated several times in order to remove or "flush" most of the residue left in the system from the proceding sample.

Thereafter, when the plunger is in its retracted position, the control unit 28 deactivates the solenoid 26 and 30 and activates a solenoid 32. Activation of the solenoid 32 brings a gear 34, driven by a synchronous motor 36, into mesh with a toothed rack 38, to thereby slowly advance the plunger 12 for sampling. This slow advancement of the plunger 12 pushes the sample out through the upper outlet 14 and through the inlet tube 16 into a heated injector 40, that is indicated by the broken line in FIG. 1, which results in continuous sample vaporization.

After a short stabilization period, the sample vapor has exactly the same composition as the liquid sample, and the vapor mass generated during a unit of time corresponds to the liquid mass introduced during the same unit of time.

In a manner similar to that disclosed in the aforesaid U.S. Pat. No. 3,668,834, the generated vapor mass is mostly rejected. In the embodiment illustrated in FIG. 1 of the present invention, this vapor mass emerges, via a line restrictor 42, into the atmosphere. However, during a definite short period of time, the vapor mass is conducted to a gas chromatographic column 44, where it is analyzed. Thereafter, the aforesaid process is repeated for the next subsequent sample. As distinguished from the aforesaid U.S. Pat. No. 3,668,834, the present invention ensures that the vapor and sample have the same composition, provided that the vaporization starts, by the introduction of the sample into the heated injector 40, a short time period before sampling.

As best seen in FIG. 1 a sampling bridge is provided, which has four arms. The first arm contains the gas chromatographic column 44 and the second arm contains the line restrictor 42, which is vented to the atmosphere. The third arm contains a tubular line 46 with a preselected flow resistance, which is connected, via a flow controller or pressure regulator 48, to a carrier gas source. The forth arm contains a second gas line 50 with a preselected, small flow resistance, that is coupled to a valve 52 which is actuated by a solenoid 53 that in turn is controlled by the control unit 28. The valve 52 is bridged by a line restrictor 54, which has a high pneumatic resistance when the valve 52 is closed. The valve 52 and the restrictor 54 are connected to a line restrictor 56, which has a small resistance. This line is connected to a junction point 58. The inlet tube 16 is coupled by means of a T-junction 59 to a supply line 60 disposed in the heated injector 40, the ends of which are connected at junction points 62 and 58 to connecting lines 64 and 66, respectively. Line 64, having adequately low flow resistance, connects tube 46 to the gas chromatographic column 44, and line 58 connects the solenoid valve 52 to the restrictor 42 through restrictor 56. Assuming the resistance of the column 44 is $R_C$, with the pneumatic resistance R being defined as $R = (p_1^2 - p_0^2/2 \, F p)$, where $p_1$ and $p_2$ represent the pressures at the two ends of the resistance, respectively, in gr. cm.$^{-1}$ sec.$^{-2}$, where F represents the flow in cm. sec.$^{-1}$, and where p represents the pressure measured at the same point as where the flow is measured (in the majority of cases the flow is measured at the beginning or the end of the column, where the pressures are $p_1$ and $p_2$ respectively), then the following resistance values have, for example, proven to be suitable;

| restrictor | 46 | 0.02 | $R_c$ |
| restrictor | 54 | 0.1 | $R_c$ |
| restrictor | 42 | 2 | $R_c$ |
| restrictor | 56 | 0.001 | $R_c$ |

When the solenoid controlled valve 52 is closed, the main carrier gas flow passes through the restrictor 46 into the column 44. A partial flow passes through the restrictor 46, via line 60, to the restrictor 42, and may carry the samples away out of line 16. For purposes of continuously flushing the upper part of line 66, a small auxiliary flow passes through the restrictor 54 into the restrictor 42.

For the purpose of column injection the solenoid valve 52 is opened for a short time interval. During this interval, the main flow passes through the valve 52, via the line 60, into the column 44, and carries with it the sample from the line 16. A partial flow passes, via the valve 52, to the restrictor 42, and a small auxiliary flow passes, via the restrictor 46, to the column 44.

In operation, switching of the solenoids 32, 26, 30 and 53 is effected by the special control unit 28, according to the following program: retracting solenoid 26 and advancing solenoid 30 are alternately energized for aspirating the next subsequent sample, and thereby flushing the instrument. When the injection command is given, after the solenoid 26 has retracted the plunger 12, the solenoid 32 is energized so that the gear 34 of the synchronous motor 36 is brought into mesh with the toothed rack 38, that is connected to the plunger 12. The motor advances the plunger so that the sample is pushed slowly and quite uniformly into the injector 40. After time of order of one second, the solenoid 53 is briefly energized for a period of from 0.01 seconds to about 0.2 seconds to feed the sample to be analyzed into the column. The aforesaid procedure is repeated for each subsequent sample.

Thus, an improved method and apparatus for introducing liquid samples into gas chromatography has been illustrated and described, which automatically introduces into a gas chromatographic column very small, medium and large sample quantities, with exact composition, in a reproducible and accurate manner. Although a specific embodiment has been illustrated and described, it will be obvious to those skilled in the art that various modifications may be made without departing from the spirit of the invention, which is intended to be limited solely by the appended claims.

What is claimed is:

1. Apparatus for introducing liquid samples into a gas chromatographic column comprising, in combination,
    means for supplying a liquid sample to a heated injector in a continuous, uniform and relatively slow-moving flow,
    means for vaporizing said sample in the heated injector,
    means for passing said vapor through a supply line in said injector to a by-passing restrictor until stationary conditions have been established, and
    means for then passing said vapor to the gas chromatographic column for sampling by reversing the flow in said supply line;
    said means for supplying a liquid sample to a heated injector in a continuous, uniform and relatively slow-moving flow comprising:

a cylinder having a dispensing outlet coupled to said supply line and an inlet coupled to a liquid sample source, a plunger mounted in said cylinder, means for rapidly reciprocating said plunger in said cylinder to aspirate in and then vent said by-passing sample through said restrictor to the atmosphere, thereby removing substantially all traces of the preceding sample, and means for slowly advancing said plunger in said cylinder to push said sample into said heated injector and thence for a relatively brief instant into said gas chromatographic column for sampling.

2. Apparatus according to claim 1 wherein said means for rapidly reciprocating said plunger in said cylinder comprises a pair of solenoid means coupled to said plunger, and wherein said means for slowly advancing said plunger in said cylinder comprises solenoid means for bringing a gear driven by a motor into engagement with a rack mounted on the plunger.

3. Apparatus for introducing liquid samples into a gas chromatographic column comprising, in combination, means for supplying a liquid sample to a heated injector in a continuous, uniform and relatively slow-moving flow, means for vaporizing said sample in the heated injector, a fluid bridge circuit having four arms including
a first arm containing said gas chromatographic column,
a second arm containing a by-passing restrictor,
a third arm containing a line restrictor, and
a forth arm containing line restriction means and means for varying the resistance of said restriction means, said heated injector having a supply line, first junction means coupling one end of said first arm with one end of said third arm and with one end of said supply line, second junction means coupling one end of said second arm with one end of said fourth arm and with the other end of said supply line, a carrier gas source coupled to the other ends of said third and fourth arms, and control means for passing said vapor through said supply line in said injector to said second arm until stationary conditions have been established and then passing it briefly through said supply line in the opposite direction to said first arm.

4. Apparatus according to claim 3 wherein said control means and said means for varying the restriction of the restrictor means in the fourth arm includes means for substantially decreasing the restriction in the fourth arm when passing said vapor through said supply line to said first arm.

5. Apparatus according to claim 4 wherein said means for substantially decreasing the resistance in the fourth arm includes a solenoid controlled valve mounted in parallel relationship with respect to a line restrictor or relatively high resistance.

6. Apparatus according to claim 5 wherein said means for supplying a liquid sample to a heated injector in a continuous, uniform and relatively slow-moving comprises, a cylinder having a dispensing outlet coupled to said supply line and an inlet coupled to a liquid sample source, a plunger mounted in said cylinder, solenoid controlled means for rapidly reciprocating said plunger in said cylinder to aspirate in and then vent said sample through said second arm to the atmosphere, thereby removing substantially all traces of the preceding sample, solenoid means for bringing a gear driven by a motor into engagement with a rack mounted on the plunger to slowly advance said plunger in said cylinder to push said sample into said heated injector and thence into said first arm for sampling, and a control unit for controlling all of said solenoids.

* * * * *